(12) United States Patent
Gurtner

(10) Patent No.: US 7,377,913 B2
(45) Date of Patent: *May 27, 2008

(54) ADJUSTMENT BLOCK FOR A DEVICE FOR ADMINISTERING A SETTABLE DOSAGE OF AN INJECTABLE PRODUCT

(75) Inventor: Thomas Gurtner, Koppigen (CH)

(73) Assignee: TecPharma Licensing AG, Burgdorf (CH)

( * ) Notice: Subject to any disclaimer, the term of this patent is extended or adjusted under 35 U.S.C. 154(b) by 558 days.

This patent is subject to a terminal disclaimer.

(21) Appl. No.: 10/638,838

(22) Filed: Aug. 11, 2003

(65) Prior Publication Data

US 2004/0030292 A1  Feb. 12, 2004

Related U.S. Application Data

(63) Continuation of application No. PCT/CH02/00061, filed on Feb. 4, 2002.

(30) Foreign Application Priority Data

Feb. 12, 2001 (DE) .............................. 101 06 368

(51) Int. Cl.
*A61M 5/00* (2006.01)
(52) U.S. Cl. .................................... 604/211
(58) Field of Classification Search ............... 604/71, 604/181, 187, 208–211, 245, 246, 248, 189, 604/220, 68, 118, 186, 207
See application file for complete search history.

(56) References Cited

U.S. PATENT DOCUMENTS

| | | | | |
|---|---|---|---|---|
| 5,112,317 A | * | 5/1992 | Michel | 604/208 |
| 5,114,406 A | * | 5/1992 | Gabriel et al. | 604/136 |
| 5,383,865 A | * | 1/1995 | Michel | 604/232 |
| 5,498,243 A | * | 3/1996 | Vallelunga et al. | 604/197 |
| 5,637,094 A | * | 6/1997 | Stewart et al. | 604/135 |
| 6,193,698 B1 | | 2/2001 | Kirchhofer et al. | |
| 6,221,046 B1 | * | 4/2001 | Burroughs et al. | 604/153 |

(Continued)

FOREIGN PATENT DOCUMENTS

EP   0 688 572 A1   12/1995

(Continued)

*Primary Examiner*—Kevin C. Sirmons
*Assistant Examiner*—Catherine N. Witczak
(74) *Attorney, Agent, or Firm*—David E. Bruhn; Dorsey & Whitney LLP

(57) ABSTRACT

A plug-on body which can be plugged onto a device for administering a settable dose of an injectable product, the plug-on body including a first body section extending axially in the direction of a plug-on body axis for fixing the plug-on body to a casing of the device, a shifting stopper formed by the first body section and operating by positive lock for axially fixing the plug-on body with respect to at least one shifting direction, a rotational stopper formed by the first body section and operating by positive lock for fixing the plug-on body against rotating, and a second body section extending behind the first body section in the direction of the plug-on body axis, wherein the second body section is formed by a shell body for at least one of shielding a dosing element of the device which serves to set the dosage and forming an adjustment stopper operating by positive lock for the dosing element.

28 Claims, 8 Drawing Sheets

U.S. PATENT DOCUMENTS

| | | | |
|---|---|---|---|
| 6,235,004 B1 * | 5/2001 | Steenfeldt-Jensen et al. | 604/207 |
| 6,394,317 B1 * | 5/2002 | Faughey et al. | 222/309 |
| 6,514,230 B1 * | 2/2003 | Munk et al. | 604/207 |
| 6,666,849 B1 * | 12/2003 | Marshall et al. | 604/246 |
| 6,699,224 B2 * | 3/2004 | Kirchhofer et al. | 604/208 |
| 6,770,056 B2 * | 8/2004 | Price et al. | 604/246 |
| 2005/0101917 A1 * | 5/2005 | Doyle | 604/187 |

FOREIGN PATENT DOCUMENTS

| | | |
|---|---|---|
| WO | WO 99/64092 | 12/1999 |

* cited by examiner

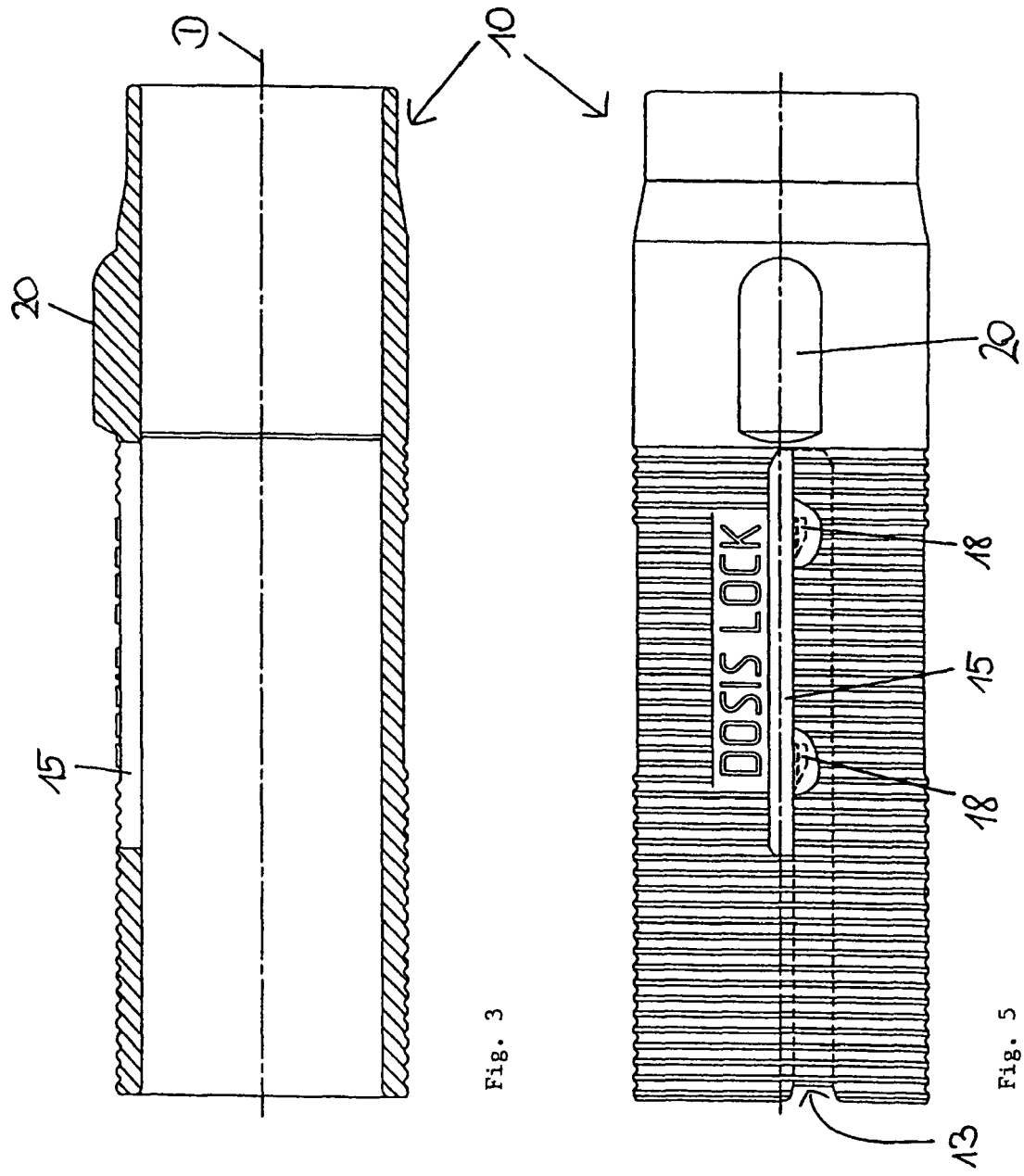

ADJUSTMENT BLOCK FOR A DEVICE FOR ADMINISTERING A SETTABLE DOSAGE OF AN INJECTABLE PRODUCT

CROSS-REFERENCE TO RELATED APPLICATION

This application is a continuation of International Patent Application PCT/CH02/00061, filed on Feb. 4, 2002, which claims priority to earlier filed German Patent 101 06 368.7, filed on Feb. 12, 2001.

BACKGROUND

The present invention relates to administering injectable products. More particularly, it relates to devices and methods for administering injectable products by means of a device on which a product dosage to be administered can be set. The product is typically a fluid that is medically and/or cosmetically effective. Insulin and growth hormones may be cited by way of example.

In general, there is a requirement not only that different product doses can be administered using the same device, but also that the product dosages can be set finely graded. In particular, in human medical applications, though in principle also in veterinary applications, the precision in setting the product dosage must be ensured with as great a reliability as possible. A particular problem with regard to administering reliability is raised by self-administering, in which a person administers a product to himself/herself. Unintentionally or even unnoticeably adjusting an already set product dosage can have serious negative consequences. Failing to accurately and clearly read the set dosage on the dosage scale of the device can also create problems.

SUMMARY

It is therefore an object of the invention to increase the reliability in administering a settable dosage of an injectable product using simple means, such that the desired product dosage is indeed administered.

In one embodiment, the invention relates to a device for administering a settable dosage of an injectable product. The device comprises a casing, a reservoir for the product formed or accommodated by the casing, a delivering means for delivering the product dosage to be administered, i.e., the set or selected product dose, from the reservoir, and a dosing and activating means connected to the casing.

The dosing and activating means fulfils the functions of setting the dosage and activating the delivering means. It is therefore connected to the casing in such a way that it can perform a dosing movement relative to the casing and a delivering movement. The product dosage is set by the dosing movement. The delivering means is activated by the delivering movement of the dosing and activating means. In some preferred embodiments, the dosing and activating means comprises a dosing element for fulfilling the function of setting the dosage and an activating element for fulfilling the function of activating the delivering means. It should not be ruled out that both functions and movements are performed by a single dosing and activating element. In some embodiments, the dosing movement and/or delivering movement may comprise the movement of a switch or a key. In some embodiments, the dosing movement is preferably a rotational movement and the delivering movement is preferably a translational movement, although the forms of movement can also be assigned the other way around. In some embodiments, the dosing movement and delivering movement can be a unitary movement, for example, a purely translational movement. In some preferred embodiments, a translational movement occurs along a rotational axis of a rotational dosing movement.

In some embodiments, the delivering means can be realized by any suitable form of pump. In some preferred embodiments, however, the delivering means comprises a piston which is accommodated in the reservoir and can be shifted towards a reservoir outlet, and which advances to deliver and administer the set product dosage through the outlet. In one preferred embodiment comprising a piston pump, the delivering means comprises a piston rod acting on the piston in the direction of the reservoir outlet. The dosing movement of the dosing and activating means reduces a gap between the piston and the piston rod. By then linearly shifting the piston rod, the piston is advanced towards the reservoir outlet and the product dosage set by adjusting the gap is delivered. The piston rod can be formed as a threaded rod which, together with a drive member provided with a counter thread, forms a spindle drive. The dosing movement of the dosing and activating means rotates the drive member relative to the casing. Via the spindle drive, and by linearly guiding the piston rod, the piston rod is moved towards the piston and the product dosage is thus set. Instead of setting the product dosage by means of a spindle drive, it could be set via a gear rack. When setting the product dosage by means of a gear rack drive, in some embodiments this is accomplished by way of a rotational movement of the dosing movement of the dosing and activating means. Examples of two ways of setting the dosage are known from DE 197 17 107 and WO 97/36626, which are referenced by way of example for their essential functionality and do not rule out other arrangements for setting the dosage and delivering the product.

The product can be administered via an infusing part, in particular an injection needle, or also without an infusing part in the form of a penetrating pressurized jet.

In one embodiment, the present invention comprises a plug-on body which can be plugged onto a device for administering a settable dosage of an injectable product, the plug-on body comprising a first plug-on body section extending axially in the direction of a plug-on body axis for fixing the plug-on body to a casing of the device, a shifting stopper formed by the first plug-on body section and operating by positive lock for axially fixing the plug-on body with respect to at least one shifting direction, a rotational stopper formed by the first plug-on body section and operating by positive lock for fixing the plug-on body against rotating, a second plug-on body section extending behind the first plug-on body section in the direction of the plug-on body axis, wherein the second plug-on body section is formed by a shell body for shielding a dosing element of the device which serves to set the dosage and/or for forming an adjustment stopper operating by positive lock for the dosing element.

In one embodiment, the present invention comprises a plug-on body which can be plugged onto a device for administering a settable dosage of an injectable product, the plug-on body comprising a first plug-on body section comprising a shifting stopper for fixing the plug-on body with respect to at least one axial direction and a rotational stopper for fixing the plug-on body against rotating, and a second plug-on body section for shielding a dosing element of the device and/or for forming an adjustment stopper for the dosing element.

In a device of the type described above, as set forth in the present invention, an adjustment block is formed by a blocking body, in that the blocking body, when connected to the casing, prevents the dosing movement of the dosing and activating means. When connected, the blocking body shields the dosing and activating means such that access to a dosing element of the dosing and activating means, which could effect an adjustment, is no longer possible. Instead of or in addition to shielding against access, the blocking body can be in a locking engagement with the casing. In one embodiment, said locking engagement may preferably be based on a positive lock which can exist between one or more longitudinal ribs, for example, a ribbing or texture, of a dosing element and the blocking body. As used herein, the term "block" is intended to include shielding alone, locking alone, a combination of shielding and locking, and/or other suitable functions.

The blocking body can be constantly connected to the casing, the connection allowing the blocking body to be moved at least once from a starting position in which a dosing movement is possible into a shielding and/or locking position in which it is no longer possible. In the case of a permanent connection, however, the blocking body preferably can be repeatedly moved back and forth between the starting position and the shielding and/or locking position.

In some preferred embodiments, a blocking body for forming the adjustment block is a separate, preferably one-piece part and is connected to the casing such that it enters into an engagement which locks the dosing movement and/or shields the dosing and activating means such that access for performing the dosing movement is no longer possible. In one preferred embodiment, the blocking body is formed such that, when connected, it can no longer be moved relative to the casing. If a locking engagement, locking the dosing movement, is formed between the blocking body and the dosing and activating means, the blocking body is sufficiently rigid, due to being itself fixed to the casing and the locking engagement, to fix the dosing and activating means relative to the casing with respect to its dosing movement. If the blocking effect of the blocking body is based on the fact that the dosing and activating means is shielded by the blocking body such that access required for performing the dosing movement is prevented, then it is in principle sufficient if connecting the blocking body to the casing ensures that the blocking body can at least not be unintentionally moved out of its shielding position. Preferably, however, in this case, the blocking body is also a rigid body.

The adjustment block in accordance with the invention is particularly advantageous in those cases in which the dosage to be administered is pre-set by a doctor and repeatedly administered by a user. In principle, the dosage can of course also be pre-set by the person wishing to administer the product dosage to himself/herself. Administering an incorrect dosage, for example, by unnoticeably adjusting the dosage, is practically ruled out.

In one embodiment, the blocking body is preferably a plug-on body which can be connected to the casing by means of a plug connection which is sufficiently stable for its blocking effect. The plug-on body is formed as a shell body and, in one preferred embodiment, as a sleeve body, which is slid over the casing and a dosing element of the dosing and activating means. A defined position of the plug-on body relative to the casing is established by one or more positively acting engaging means on the plug-on body and on the casing. It is advantageous if a latching connection is formed between the casing and the plug-on body. The latching connection can form the plug connection between the plug-on body and the casing by itself. The latching connection can also ensure that the plug-on body is held in positive engagement with the casing, such that the latching connection firstly has to be released in order to release the positive engagement and thus be able to remove the plug-on body from the casing.

As compared to a blocking body formed integrally on the device, a separate blocking body has the advantage that no costly modifications have to be made to devices without an adjustment block. This can be advantageous when devices which have hitherto been produced without an adjustment block are to be fitted with an adjustment block. Modifications in production due to one or more engaging means which possibly have to be provided on the casing can be made at comparatively little cost. In particular, modifications to moving parts of the dosing and activating means are not required or only to a small extent. Moreover, it is perfectly possible to form the blocking body such that recesses, indentations or protrusions and the like, already provided on the respective casing, can be used for a positive engagement with the casing, and one or more corresponding engaging elements can be formed on the plug-on body.

The idea of locking the dosing movement of the dosing and activating means by means of a separate plug-on body or of correspondingly shielding the dosing and activating means, wherein the two can also be used with preferred plug-on bodies in combination, results in another embodiment of the invention for providing a reading aid. The reading aid relates to the same device as the adjustment block. In a basic form of the reading aid, the plug-on body is modified to the effect that with the aid of it, a blocking effect with respect to the dosing movement of the dosing and activating means does not have to but can advantageously be realized. As compared to a plug-on body whose blocking effect is based solely on shielding a dosing element, a shielding blocking body section provided with the blocking body can be replaced by a plug-on body section which forms a reading-glass, in order to be able to more easily and therefore more reliably read the possibly very fine characters of a dosage scale. Moreover, the plug-on body can advantageously be adopted unaltered from the adjustment block. Combining an adjustment block with a reading aid is particularly advantageous.

If the dosing element of the dosing and activating means is provided with the dosage scale, as is usual, then the plug-on body forming the reading aid is fixedly connected to the casing, such that the reading-glass comes to rest above the dosage scale of the dosing element. If the casing is provided with the dosage scale, the plug-on body is fastened to the dosing element performing the dosing movement, such that the reading-glass participates in the dosing movement and is thus moved over the dosage scale. In the case of an adjustment block based on locking engagement, a blocking body can also be fastened to the dosing element and a locking engagement formed with the casing.

In one embodiment, the present invention comprises a plug-on body which can be plugged onto a device for administering a settable dosage of an injectable product, said plug-on body comprising:

a) a first plug-on body section, extending axially in the direction of a plug-on body axis (D), for fixing the plug-on body to a dosing element which serves to set the dosage or preferably to a casing of said device;

b) a shifting stopper, formed by said first plug-on body section and operating by positive lock, for axially fixing the plug-on body with respect to at least one shifting direction;

c) a rotational stopper, formed by the first plug-on body section and operating by positive lock, for fixing the plug-on body against rotating;

d) and a second plug-on body section, extending behind the first plug-on body section in the direction of said plug-on body axis (D), e) wherein said second plug-on body section forms a reading-glass for reading a dosage scale of the device and, when connected, to a reading aid of a device for administering a settable dosage of an injectable product, said device comprising:

a) a casing;

b) a reservoir, formed or accommodated by the casing, from which a product dosage is administered;

c) a delivering means for delivering the product dosage to be administered from said reservoir;

d) a dosing and activating means, connected to the casing, with which a dosing movement for setting a product dosage can be performed relative to the casing and the delivering means can be activated;

e) and a plug-on body which forms a reading-glass through which a dosage scale of the device can be read, when the plug-on body is connected to the casing or to the dosing and activating means.

BRIEF DESCRIPTION OF THE DRAWINGS

The invention will now be explained by way of exemplary preferred embodiments.

FIG. 3 depicts the plug-on body of FIG. 1, in a longitudinal section;

FIG. 4 depicts the plug-on body in a cross-section;

FIG. 5 depicts the plug-on body in a view;

DETAILED DESCRIPTION

Figure 1:
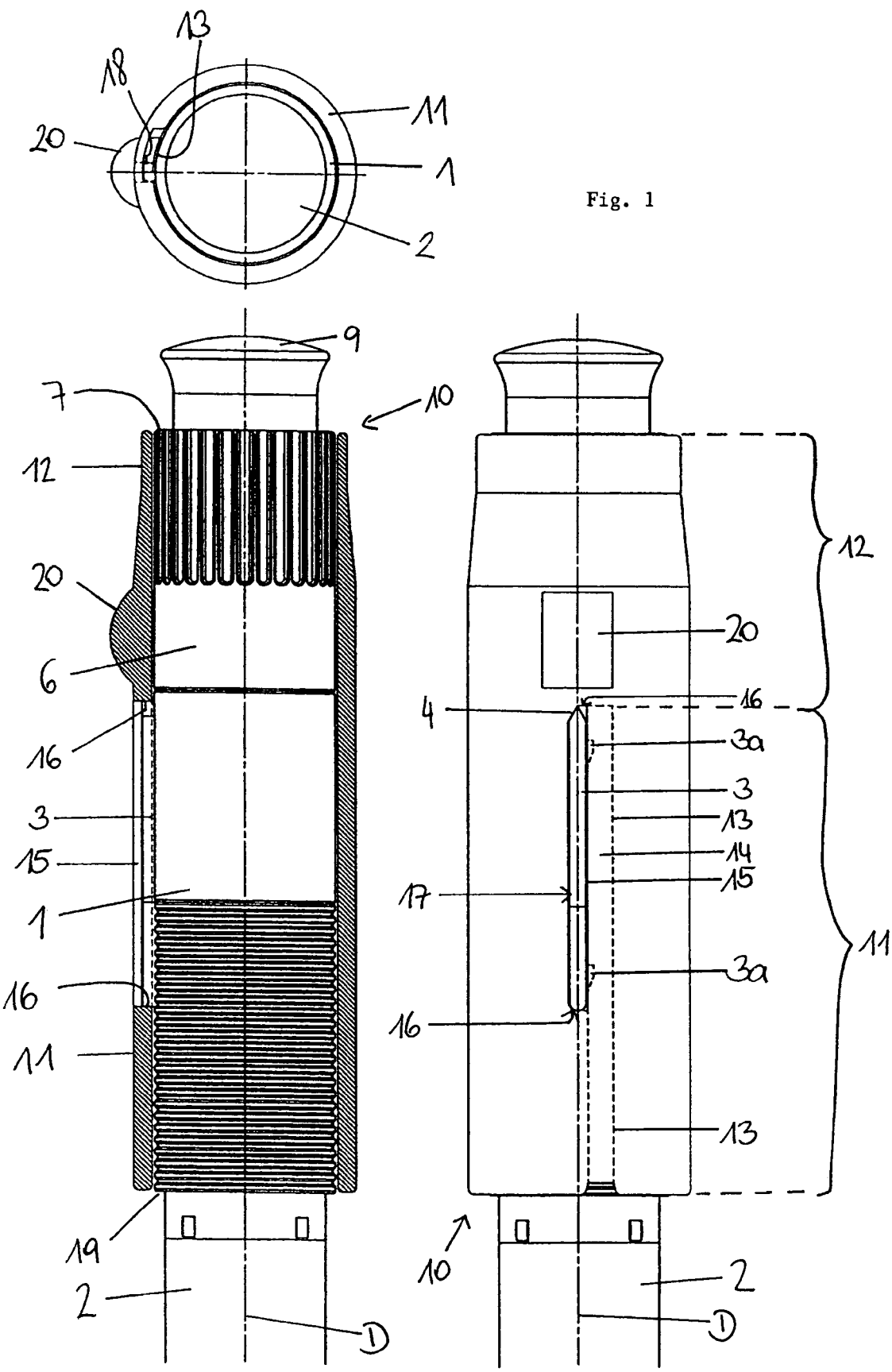
FIG. 1 depicts an adjustment block, formed by a plug-on body fastened to an injection apparatus, as set forth in a first exemplary embodiment.
Figure 2:
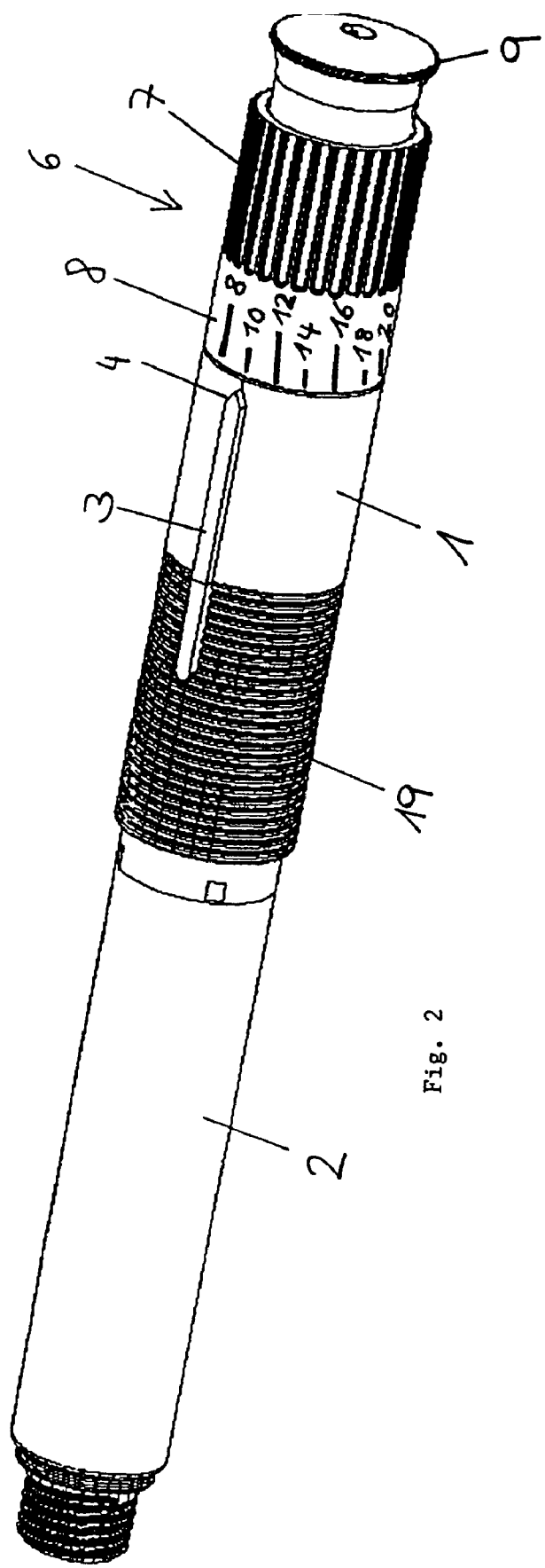
FIG. 2 depicts the injection apparatus of FIG. 1.

FIG. 1 shows a view, a longitudinal section and a top view of an adjustment block which is formed on an injection apparatus comprising a plug-on body 10. Only a rear part of the injection apparatus, which in this examplary embodiment is a so-called injection pen, is illustrated, the plug-on body 10 having been coupled to, slid over or plugged onto said rear part. The injection apparatus is shown in FIG. 2, except for its foremost part, without the plug-on body 10. FIGS. 3 to 5 show a plug-on body 10 which deviates from the plug-on body 10 of FIG. 1. The plug-on body 10 of FIG. 1 can be directly replaced by the plug-on body 10 of FIGS. 3 to 5. The first exemplary embodiment is therefore described in an overview of FIGS. 1 to 5.

The injection apparatus (FIG. 2) comprises an ampoule holder 2 and a guiding part 1 connected to the ampoule holder 2, secured against rotating and shifting, which in the sense of the invention are regarded as the casing of the injection apparatus. The ampoule holder 2 serves to accommodate an ampoule filled with a product to be administered, for example insulin. A dosing and activating means forms the rearmost part of the injection apparatus and is supported by the guiding part 1 such that it can perform a dosing movement for setting a product dosage to be administered and a delivering movement for activating a delivering means. The dosing and activating means comprises a dosing element 6 and an activating element 9. The sleeve-shaped dosing element 6 can be rotated about its central longitudinal axis, relative to the guiding part 1. The dosing movement is a rotational movement of the dosing element 6 about the rotational axis D formed by the central longitudinal axis. The activating element 9 can be shifted back and forth along the rotational axis D of the dosing element 6, relative to the guiding part 1 and relative to the dosing element 6. By shifting the activating element 9 backwards, the ampoule can be raised, i.e. filled with new product. Shifting the activating element 9 towards the front end of the injection apparatus activates the delivering means. To set the product dosage, the dosing element 6 acts, via a spindle drive or a gear rack drive, such as are presumed to be known in principle, on a piston rod which is shifted along the rotational axis D, relative to the guiding part 1 and the ampoule holder 2, by the dosing movement of the dosing element 6. In particular, the dosing movement linearly shifts the piston rod and reduces a slight gap between a piston accommodated in the ampoule and a front active end of the piston rod, setting a product dosage which may be delivered by a subsequent delivering movement of the activating element 9.

The dosing element is provided with a grip aid 7 which is formed as a ribbing comprising linear ribs extending in the direction of the rotational axis D. On the dosing element 6, a dosage scale 8 is printed on the circumference of an end facing the guiding part 1, said dosage scale 8 in combination with a marking arrow 4 enabling the product dosage set to be read. The marking arrow 4 is arranged opposite the dosage scale on a rear end of the guiding part 1 and is fixedly connected to the guiding part 1. The marking arrow 4 forms a rear end of a protrusion 3 which radially projects from an outer surface area of the guiding part 1. In the exemplary embodiment, the protrusion 3 including its rear end forming the marking arrow 4 is formed as a linear rib extending in the direction of the rotational axis D of the dosing element 6.

The protrusion 3 forms an engaging means of the casing for fixing the plug-on body 10. FIG. 1 shows the injection apparatus and the plug-on body 10 after a connection has been established in which the plug-on body 10 is connected axially, i.e., in the direction of the rotational axis D of the dosing element 6, to the guiding part 1, and secured against rotating with respect to said rotational axis D.

In the exemplary embodiment, the plug-on body 10 is formed by a sleeve body which is shaped in strict adjustment with the outer shape of the injection apparatus, in particular the guiding part 1. As a whole, the sleeve body forms a hollow cylinder. The plug-on body 10 comprises a first plug-on body section 11 and a second plug-on body section 12 in a row in the longitudinal direction. The first plug-on body section 11 fulfils the function of fastening to the casing. The second plug-on body section 12 fulfils the function of shielding the dosing element 6 against access, through which a dosing movement of the dosing element 6 could be performed, and the dosing element 6 thus adjusted. The second plug-on body section 12 is a continuous sleeve part and surrounds the dosing element 6 along its entire length. The second plug-on body section 12 need not necessarily be formed as a closed sleeve, but may indeed comprise breaches, although the dosing element 6 must be secured against unintentional access by being inadvertently handled, for example by children, if the blocking effect of the plug-on body 10 is based solely on shielding the dosing element 6, as in this exemplary embodiment. In addition to shielding, the plug-on body 10 can also be formed for a locking engagement with the dosing element 6.

The first plug-on body section 11 forms two shifting stoppers 16, which operate by positive lock and prevent the plug-on body 10 from moving along the rotational axis D of the dosing element 6 in either direction. It furthermore forms a rotational stopper 17 which operates by positive lock and prevents the plug-on body 10 from rotating about the rotational axis of the dosing element 6 with respect to a rotational direction. Relative rotation in the opposite direction with respect to the casing is prevented by means of a detachable latching connection.

For forming the cited stoppers 16 and 17 and the latching connection, the plug-on body 10 is provided in the first plug-on body section 11 with a recess 13 on an inner surface area. The recess 13 is a blind recess. The recess 13 extends from a front facing side of the plug-on body 10 in the direction of the longitudinal axis of the plug-on body 10. When it is connected to the casing, the longitudinal axis of the plug-on body 10 is parallel to the rotational axis D of the dosing element 6; preferably, it corresponds to the rotational axis D of the dosing element, as in the exemplary embodiment. Viewed in the circumferential direction of the plug-on body 10, the recess 13 is sufficiently wide over its entire length to be able to accommodate the protrusion 3 formed on the guiding part 1. Viewed in the circumferential direction, the recess is widened in a rear area which forms a rear end of the recess 13. The widening 15 of the recess 13 thus formed comprises radial limiting walls which form the shifting stoppers 16 and the rotational stopper 17 of the plug-on body 10. The limiting wall forming the rotational stopper 17 extends in the longitudinal direction of the plug-on body 10. The limiting walls facing opposite each other and forming the shifting stoppers 16 extend in the circumferential direction of the plug-on body 10. When it is connected, the protrusion 3 of the casing in the widening 15 is simultaneously pressed onto the rotational stopper 17 and the shifting stoppers 16.

In order to prevent a reverse rotational movement which is not locked by the stoppers 16 and 17 on the plug-on body side, the plug-on body 10 may be provided with at least one latching element, for example, as depicted in FIG. 5, two latching elements 18. The latching elements 18 cooperate in pairs with latching elements 3a formed on the casing, by forming a detachable latching connection with the latching means 3a.

A reading-glass 20 is formed in the area of the second plug-on body section 12. The reading-glass 20 is arranged directly behind the widening 15, viewed in the direction of the longitudinal axis of the plug-on body 10, such that once the plug-on body 10 has been fixed to the casing, the reading-glass 20 is above the dosing scale 8 of the dosing element 6 and the dosage scale 8 can be read through the reading-glass 20. Optical magnification by the reading-glass 20 makes it easier to read the dosage scale 8 and thus also makes setting the product dosage more reliable. Once the plug-on body 10 has been fixed, the tip of the marking arrow 4 points to the center of the reading-glass 20.

The part of the recess 13 forming the blind groove which extends as far as the front facing area of the plug-on body 10 is not shaped as an breach but rather as a cavity 14 in the first plug-on body section 11. The widening 15 forming the shifting stopper 16 and the rotational stopper 17 of the plug-on body 10 breaches the second plug-on body section 12 over its entire area, such that when connected, the marking arrow 4 is clearly visible. The part of the recess 13 formed as a cavity 14 can in principle also be formed as a breach. It would be equally conceivable to form the widening 15 as a cavity. In addition to being easier to read, however, forming it as a breach also has manufacturing advantages, when the plug-on body 10 is manufactured as a plastic injection-molded part, as may be preferred.

The plug-on body 10 can be manufactured, in its entirety or to a large extent, from a transparent material, such that the dosage scale 8 of the dosing element 6 is inherently visible, even without forming a reading-glass 20. If the plug-on body 10 consists of an opaque material, the reading-glass 20 can also be replaced by a viewing window, through which the dosage scale 8 is not magnified.

If a plug-on body, manufactured in its entirety or to a large extent from a transparent material, forms the reading aid, then the plug-on body as a whole or the large transparent area can be formed such that the magnified dosage scale 8 of the dosing element 6 is inherently readable, without forming the reading-glass as a partial area. If the plug-on body is formed from an opaque material, then the reading-glass 20 or a simple viewing window can be employed or, for example while still manufacturing the plug-on body 10 as an injection-molded part, can be transfused with the plug-on body material in the injection mold.

In the exemplary embodiment, a ribbing 19 for increasing the grip of the injection apparatus is provided in a front area of the guiding part 1 and is covered by the first plug-on body section when connected. Instead or equally, a ribbing which increases the grip can be formed on the outer side of the plug-on body section 11. FIGS. 3 to 5 show such a plug-on body 10 by way of example. As can also be seen in FIGS. 4 and 5, each of the latching means 18 is formed by a latching projection on a surface area of the plug-on body 10. The latching elements 18 are shaped as latching projections which project radially inwards. The latching means 3a of the casing are also formed by latching projections which slide over the latching projections 18 and snap in behind the latching elements 18 in order to establish the latching connection. The latching elements 18 or the latching elements 3a could also be shaped as pockets into which the latching projections snap. A single latching element or more than two latching elements can be formed on each of the plug-on body 10 and the casing, in order to establish the latching connection.

Mounting the plug-on body 10 of the first exemplary embodiment on the casing of the injection apparatus is very easily possible via the dosing and activating means, which comprises the dosing element 6 and activating element 9. Once the desired product dosage has been set by rotating the dosing element 6, the plug-on body 10 is slid over the activating element 9 and the dosing element 6 onto the casing from the rear. Because of the small radial gap from the dosing element 6 and the casing, the recess 13 has to be brought flush with the protrusion 3 in order to slid the plug-on body 10 on, such that through the protrusion 3 engaging with the recess 13, the plug-on body 10 is linearly guided in the direction of the rotational axis D of the dosing element 6 as it is slid on. The plug-on body 10 is slid on until the reverse end of the protrusion 3, formed by the marking arrow 4, comes to rest against the rear shifting stopper 16 of the plug-on body 10. The sliding-on process is then complete. In this shifting position, the plug-on body 10 and the injection apparatus are rotated about the rotational axis D relative to each other, such that the protrusion 3 comes to rest against the rotational stopper 17. Due to the specific shape of the protrusion 3 as a linear rib and of the widening 15 as a linear recess adjusted in its shape to the protrusion 3, the protrusion 3 is accommodated in the widening 14 such that it also has contact with the front shifting stopper 16. At the same time as the stopper position is reached with respect to the rotational movement, the latching elements 3a of the injection apparatus and the latching elements 18 of the plug-on body 10 latch with each other. In this moment, the plug-on body 10 is fixed to the injection apparatus such that it cannot be shifted or rotated, wherein the fixture via the shifting stoppers 16 and the fixture via the rotational stopper 17 is fixed, and the fixture via the latching connection 3a, 18 is releasable.

Figure 6:
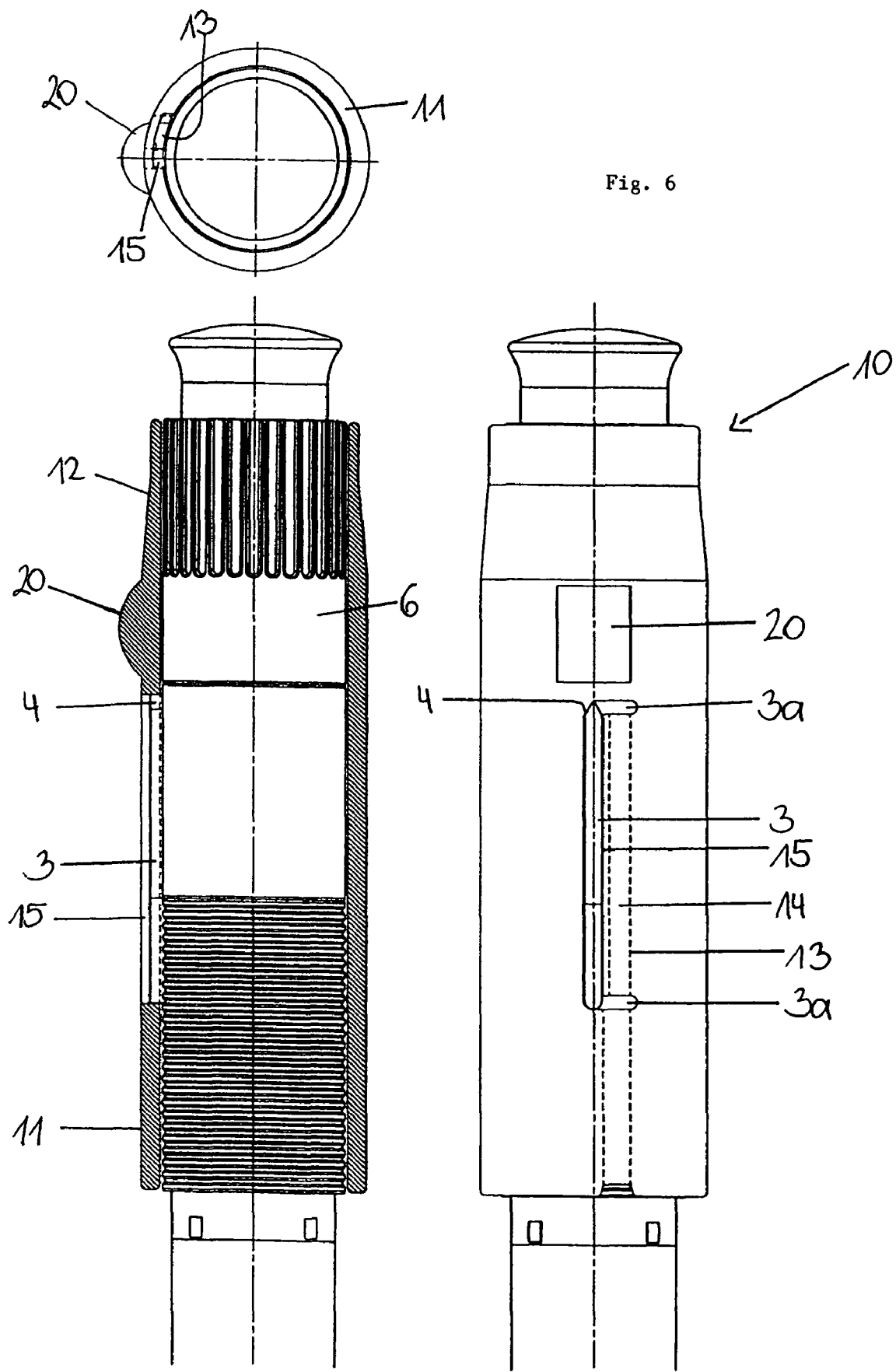
FIG. 6 depicts the injection apparatus comprising a plug-on body as set forth in a second exemplary embodiment.

The second exemplary embodiment of an adjustment block and reading aid, shown in FIG. 6, differs from the first exemplary embodiment with respect to the latching connection. The latching elements 3a and 18 of the second exemplary embodiment are larger than those of the first exemplary embodiment. This results in a more stable latching connection, which requires a larger force to be employed to release it.

Figure 7:
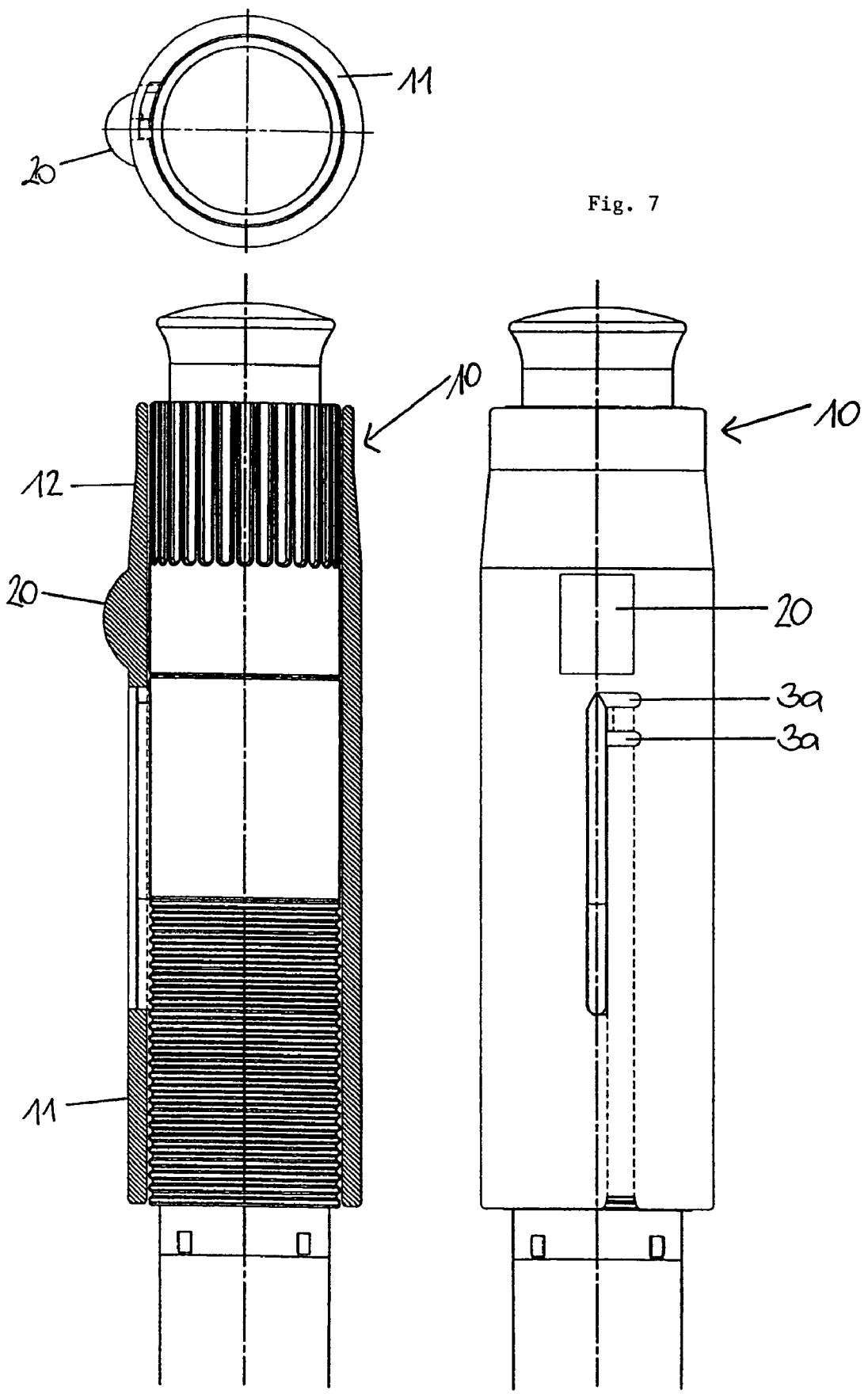
FIG. 7 depicts the injection apparatus comprising a plug-on body as set forth in a third exemplary embodiment.

The third exemplary embodiment shown in FIG. 7 generally corresponds to the second exemplary embodiment, the position of the latching elements 3a and 18 being varied as compared to the second exemplary embodiment. By varying the axial gap between the latching elements 18 on the one hand and between the latching elements 3a on the other, the spring forces acting for the latching connection can be varied.

Figure 8:
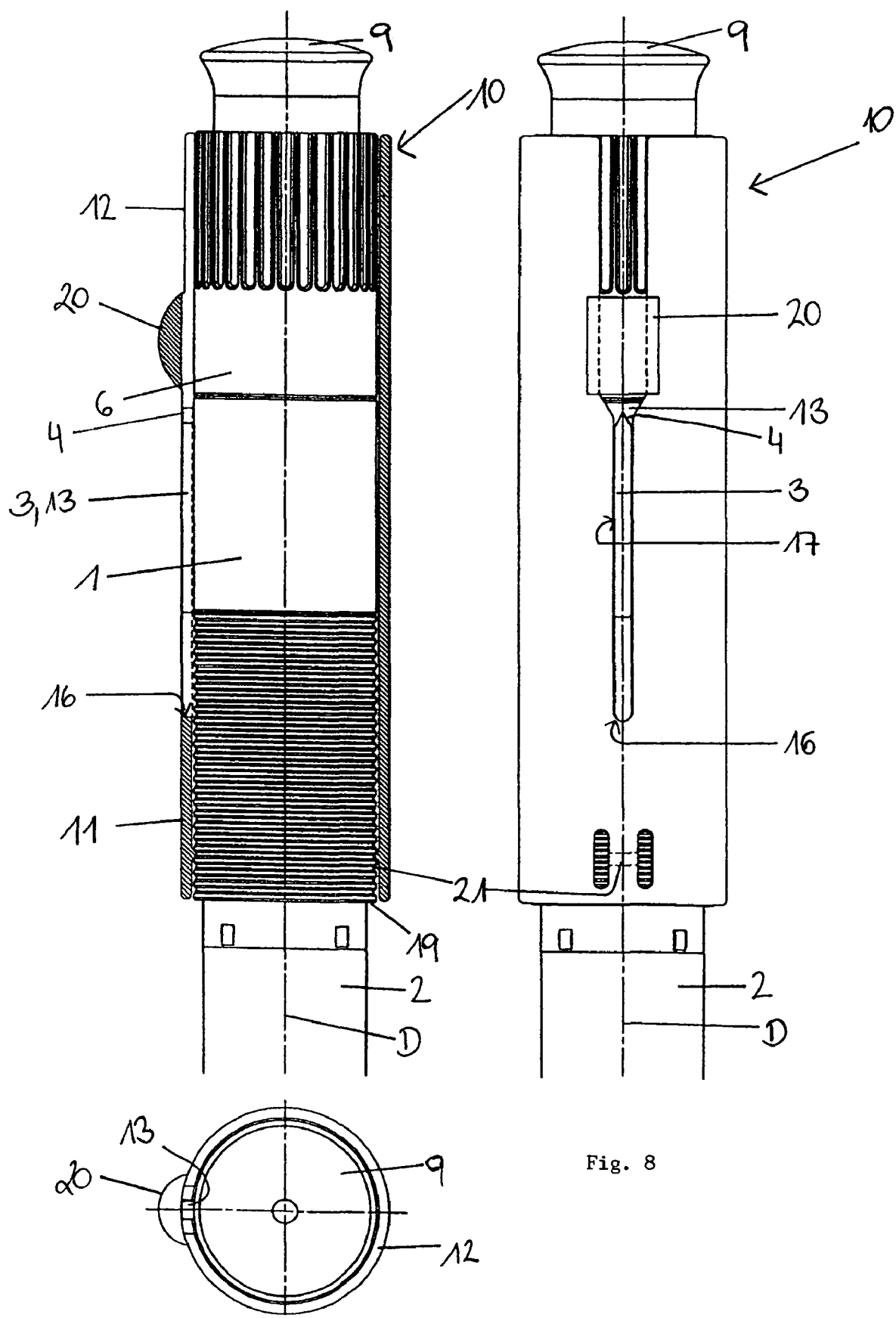
FIG. 8 depicts the injection apparatus comprising a plug-on body as set forth in a fourth exemplary embodiment.

FIG. 8 shows an injection apparatus/plug-on body combination in accordance with the present invention in a fourth exemplary embodiment. The plug-on body 10 is again formed as a sleeve body. The functions of the plug-on body 10, namely fixing to the casing and preventing the dosing movement of the dosing element 6, include at least the same functions as in the plug-on bodies 10 of the embodiments already described.

The plug-on body 10 of the fourth exemplary embodiment, however, is not slid on via the activating element 9 but rather via the front end of the injection apparatus. In order to enable it to be slid on from the front, the recess 13 extends in the longitudinal direction of the plug-on body 10 as far as the rear facing side of the plug-on body 10. In order to enable a good view of the marking arrow 4, the recess 13 is formed from its rear end up to its front end as a breach which is covered by the reading-glass 20 arranged above it. The recess 13 forms a rotational stopper 17 acting in both directions and a shifting stopper 16 acting in a sliding direction, namely the sliding-on direction. Inadvertently retracting the plug-on body 10 to the front end of the injection apparatus is prevented by a latching connection.

The latching connection is established in this exemplary embodiment with the aid of the ribbing 19 provided on the guiding part 1. A latching element 21 is formed on the plug-on body 10, between two closely spaced breaches adjacent to each other in the circumferential direction, near a front end of the first plug-on body section 11. The surface area of the plug-on body between the two breaches is swelled radially inwards and forms an elastically flexible latching element 21 due to the two breaches. In this exemplary embodiment, two such latching elements 21 are formed diametrically opposite each other in the first plug-on body section 11. They engage with the circumferential grooves of the ribbing 19 of the guiding part 1, wherein the engagement can however be released due to the spring elasticity of the latching elements 21, by exerting a sufficient shifting force in the direction of the front end of the injection apparatus.

Figure 9:
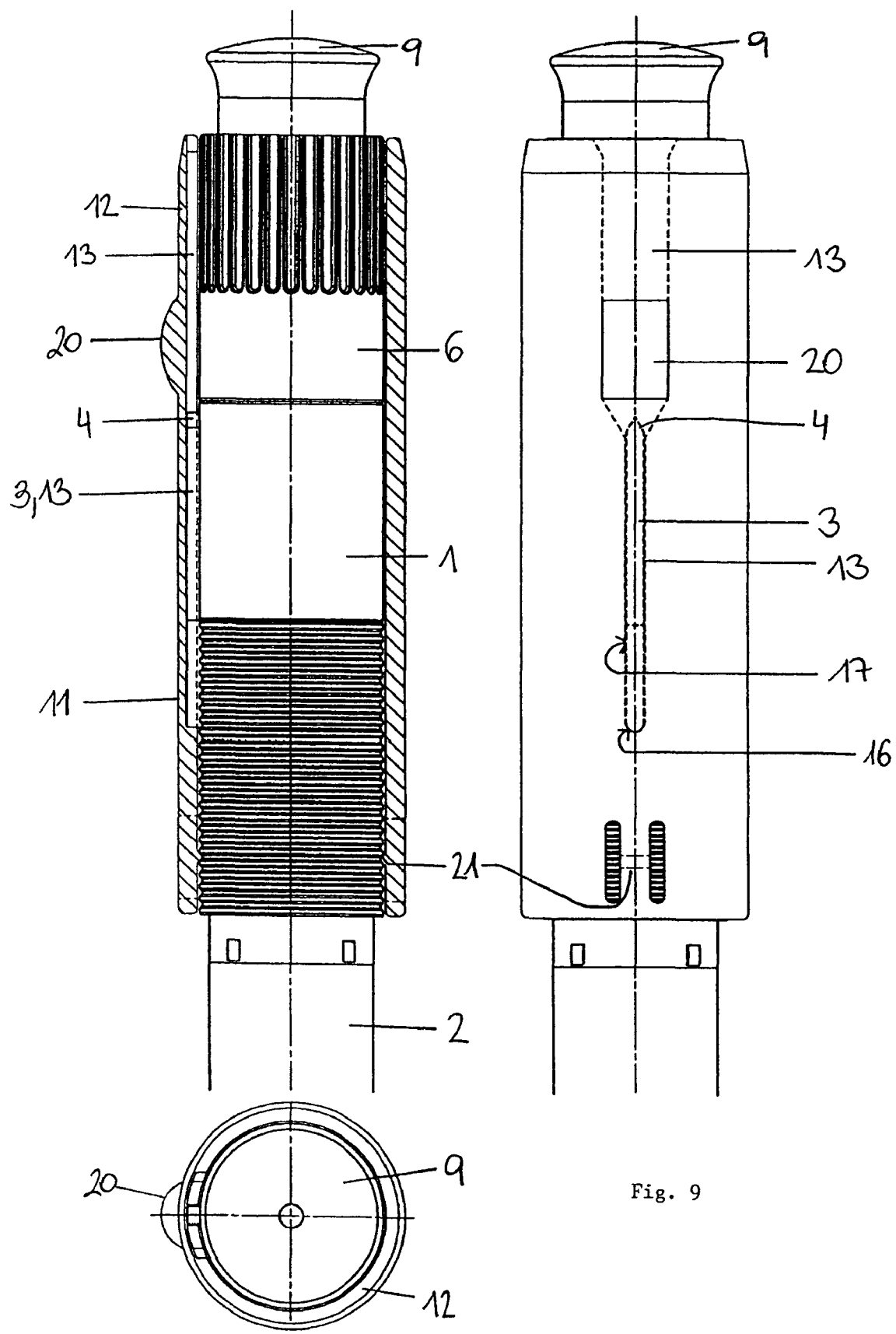
FIG. 9 depicts the injection apparatus comprising a plug-on body as set forth in a fifth exemplary embodiment.

FIG. 9 shows an adjustment block and reading aid as set forth in a fifth exemplary embodiment. The plug-on body 10 of this exemplary embodiment is substantially identical to the plug-on body 10 of FIG. 8. Unlike the exemplary embodiment in FIG. 8, however, the recess 13 is not formed as a breach but rather as a cavity on the inner surface area of the plug-on body 10. In order to form a defined rotational stopper 17, the wall thickness of the plug-on body 10 is correspondingly greater than in the preceding exemplary embodiment.

Figure 10:
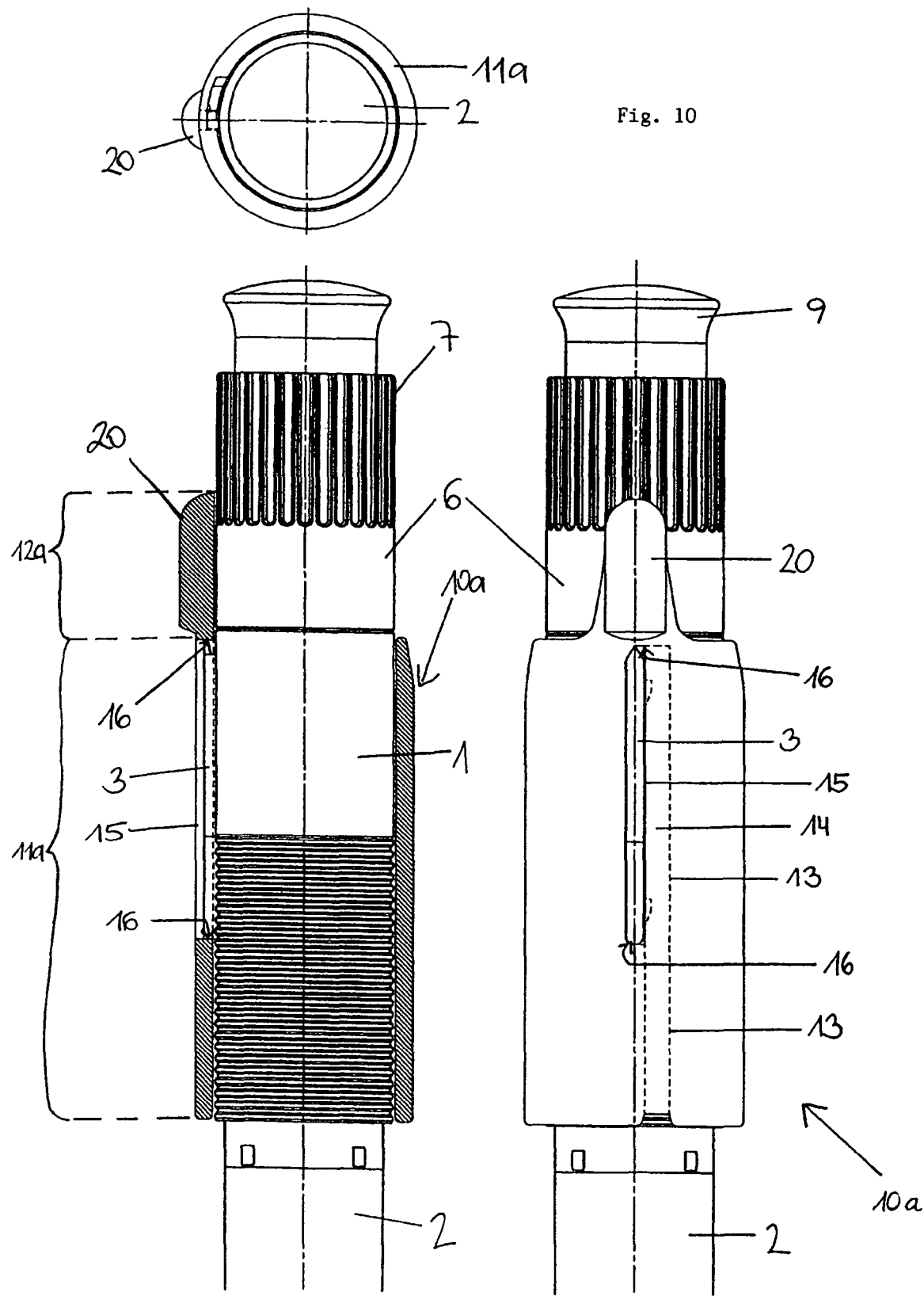
FIG. 10 depicts the injection apparatus comprising a reading aid formed by a plug-on body.

FIG. 10 shows a reading aid formed by a plug-on body 10a which is derived from the plug-on body 10 of the first exemplary embodiment but does not perform a blocking function. The plug-on body 10a corresponds to the plug-on body 10 of the first exemplary embodiment in its first section 11, such that in this respect reference may be made to the description of the first exemplary embodiment. The second plug-on body section 12a, however, forms only the reading-glass 20 of the first exemplary embodiment and in this respect is achieved by reducing the second plug-on body section 12 of the first exemplary embodiment to the magnifying function, and also geometrically as a reduction to the reading-glass 20 which axially extends the first plug-on body section 11 like a tongue. The plug-on body 10a shows that the idea of the plug-on body which may be fastened to the casing of an injection apparatus, secured against shifting and rotating, can be used flexibly to fulfill additional functions employed in the sense of the invention to increase dosing reliability.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A plug-on body positioned on a device to administer an injection, the device having an outer casing, a rotatable dosing mechanism to select a dose amount to be administered, an activating element to initiate administration of the injection, and a protrusion formed on the surface of the outer casing, the plug-on body comprising:

a) a first plug-on body section positioned on the outer casing of the device and having an elongated groove extending the length of the first plug-on body section along a longitudinal axis of the device, wherein the elongated groove has a narrow portion to slide on the protrusion formed on the surface of the outer casing of the device and a widened portion to accommodate the protrusion to lock the plug-on body to prevent axial and rotational movement of the plug-on body in relation to the outer casing of the device;

b) and a second plug-on body section fixedly attached to the first plug-on-body section and positioned proximal to the activating element of the device, wherein the second plug-on body section extends over the rotatable dosing mechanism of the device, to prevent adjustment of the rotatable dosing mechanism of the device.

2. The plug-on body as set forth in claim 1, wherein the second plug-on body section is formed by a shell body.

3. The plug-on body as set forth in claim 2, wherein said shell body is a sleeve body.

4. The plug-on body as set forth in claim 1, wherein the first plug-on body section is formed by a shell body provided with a recess which forms the elongated groove.

5. The plug-on body as set forth in claim 4, wherein said recess of the first plug-on body section extends as far as a facing side of the plug-on body.

6. The plug-on body as set forth in claim 5, wherein the recess is a blind recess.

7. The plug-on body as set forth in claim 5, wherein the walls of a widened portion of the recess substantially perpendicular to the longitudinal axis of the device prevent movement of the plug-on body with respect to the outer casing of the device along the longitudinal axis of the device.

8. The plug-on body as set forth in claim 7, wherein a wall of the recess substantially parallel to the longitudinal axis of the device prevents rotational movement of the plug-on body with respect to the outer casing of the device around the longitudinal axis of the device.

9. The plug-on body as set forth in claim 4, wherein the first plug-on body section is provided with at least one latching element for establishing a latching connection with the outer casing of the device.

10. The plug-on body as set forth in claim 9, wherein said at least one latching element is formed in the recess.

11. The plug-on body as set forth in claim 1, wherein the plug-on body is transparent in at least one area, the transparent area for forming a viewing window being arranged such that once the plug-on body has been fixed, a dosage scale of the device can be read.

12. The plug-on body as set forth in claim 11, wherein said viewing window forms a reading-glass.

13. A plug-on body positioned on a device to administer an injection, the device having an outer casing, a rotatable dosing mechanism for selecting a dose amount to be administered, an activating element for initiating administration of the injection, and a protrusion formed on the surface of the outer casing to cooperate with the rotatable dosing mechanism to enable selection of the dose amount, the plug-on body comprising:

a) a first plug-on body section on the outer casing of the device and having an elongated groove extending the length of the first plug-on body section along a longitudinal axis of the device, wherein the elongated groove has a first portion to slide on the protrusion formed on the surface of the outer casing of the device and a second portion to accommodate the protrusion to lock the plug-on body to prevent axial and rotational movement of the plug-on body in relation to the outer casing of the device; and b) a second plug-on body section fixedly attached to the first plug-on-body section and positioned proximal to the activating element of the device, wherein the second plug-on body section extends over the rotatable dosing mechanism of the device to prevent adjustment of the rotatable dosing mechanism of the device.

14. The plug-on body as set forth in claim 13, wherein the second plug-on body section is formed by a shell body.

15. The plug-on body as set forth in claim 14, wherein said shell body is a sleeve body.

16. The plug-on body as set forth in claim 13, wherein the first plug-on body section is formed by a shell body provided with a recess which forms the elongated groove.

17. The plug-on body as set forth in claim 16, wherein said recess of the first plug-on body section extends as far as a facing side of the plug-on body.

18. The plug-on body as set forth in claim 17, wherein the recess is a blind recess.

19. The plug-on body as set forth in claim 17, wherein the walls of a widened portion of the recess substantially perpendicular to the longitudinal axis of the device prevent movement of the plug-on body with respect to the outer casing of the device along the longitudinal axis of the device.

20. The plug-on body as set forth in claim 19, wherein a wall of the recess substantially parallel to the longitudinal axis of the device prevents rotational movement of the plug-on body with respect to the outer casing of the device around the longitudinal axis of the device.

21. The plug-on body as set forth in claim 16, wherein the first plug-on body section is provided with at least one latching element for establishing a latching connection with the outer casing of the device.

22. The plug-on body as set forth in claim 21, wherein said at least one latching element is formed in the recess.

23. The plug-on body as set forth in claim 13, wherein the plug-on body is transparent in at least a local area, the transparent area for forming a viewing window being arranged such that once the plug-on body has been fixed, a dosage scale of the device can be read.

24. The plug-on body as set forth in claim 23, wherein said viewing window forms a reading-glass.

25. A device for administering a settable dosage of an injectable product, said device comprising:

a) a casing;

b) a reservoir, formed or accommodated by the casing, from which a product dosage is administered;

c) a delivering means for delivering the product dosage to be administered from said reservoir;

d) an activating means, connected to the casing, with which the delivering means can be activated;

e) a rotating dosing means for selecting a dose amount to be administered;

f) a protrusion formed on the surface of the casing; and g) a plug-on body which prevents the dosing movement of the rotating dosing means, wherein the plug-on body has an elongated groove extending along a longitudinal axis of the device, and wherein the elongated groove has a first portion for accommodating the protrusion formed on the surface of the outer casing of the device and a second portion for accommodating the protrusion to lock the plug-on body to prevent axial and rotational movement of the plug-on body in relation to the casing of the device, thereby preventing adjustment of the rotating dosing means of the device.

26. The device according to claim 25, wherein the plug-on body comprises:

a first plug-on body section comprising a shifting stopper for fixing the plug-on body with respect to at least one axial direction and a rotational stopper for fixing the plug-on body against rotating; and a second plug-on body section forming an adjustment stopper for the dosing means.

27. The device according to claim 25, wherein the plug-on body comprises:
a first plug-on body section comprising a shifting stopper for fixing the plug-on body with respect to at least one axial direction and a rotational stopper for fixing the plug-on body against rotating; and
a second plug-on body section shielding a dosing element of the dosing means.

28. The plug-on body according to claim 27, wherein the second plug-on body section also forms an adjustment stopper for the dosing element.

* * * * *